United States Patent [19]

Vignaud et al.

[11] Patent Number: 5,176,680
[45] Date of Patent: Jan. 5, 1993

[54] DEVICE FOR THE ADJUSTABLE FIXING OF SPINAL OSTEOSYNTHESIS RODS

[76] Inventors: Jean-Louis Vignaud, 10 impasse Francois Audouin, 33400 Talence; Philippe Lapresle, 32 boulevard Victor Hugo, 92200 Neuilly sur Seine; Jean-Francois Sacriste, 5 square Maurice Ravel la Chapelle Forestière, 33115 Le Pyla sur Mer; Gilles Missenard, 94-96 quai Louis Blériot, 75016 Paris, all of France

[21] Appl. No.: 652,101

[22] Filed: Feb. 8, 1991

[30] Foreign Application Priority Data

Feb. 8, 1990 [FR] France ............... 90 01634
Mar. 19, 1990 [FR] France ............... 90 03694

[51] Int. Cl.⁵ ............................. A61F 2/00
[52] U.S. Cl. ........................... 606/61; 606/60; 606/73
[58] Field of Search .................. 606/54-62, 606/64, 72, 73

[56] References Cited

U.S. PATENT DOCUMENTS

| | | | |
|---|---|---|---|
| 4,483,334 | 11/1984 | Murray | 606/59 |
| 4,502,473 | 3/1985 | Harris et al. | 606/59 X |
| 4,887,596 | 12/1989 | Sherman | 606/73 X |
| 4,946,458 | 8/1990 | Harms et al. | 606/72 X |
| 5,047,029 | 9/1991 | Aebi et al. | 606/59 X |
| 5,067,955 | 11/1991 | Cotrel | 606/61 |

FOREIGN PATENT DOCUMENTS

| | | | |
|---|---|---|---|
| 0408489 | 1/1991 | European Pat. Off. | 606/72 |
| 3722590 | 12/1988 | German Democratic Rep. | 606/61 |
| 9101691 | 2/1991 | World Int. Prop. O. | 606/61 |

Primary Examiner—Richard J. Apley
Assistant Examiner—Linda C. M. Dvorak
Attorney, Agent, or Firm—Roylance, Abrams, Berdo & Goodman

[57] ABSTRACT

The present invention concerns a device for fixing osteosynthesis rods to pedicular screws (1), the device being of the type including a diapason-shaped head (4) defining two branches (4a, 4b) collectively receiving a rod (6) to be fixed, the head being locked in its housing (5) by a locking screw (7), wherein it further includes, threaded on the rod (6) and inserted between the locking screw (7) and the bottom of the housing (5), a split ring (9) whose opposing external faces (10) directed towards the locking screw (7) and said bottom are convex and received in complementary concave surfaces (11, 12) provided on the extremity of the locking screw (7) and the bottom of the receiving housing (5) of the rod (6), the ring (9), prior to locking of the screw (7), allowing for a certain angular clearance of the rod (6) with respect to the axis of the screw (1).

16 Claims, 2 Drawing Sheets

DEVICE FOR THE ADJUSTABLE FIXING OF SPINAL OSTEOSYNTHESIS RODS

FIELD OF THE INVENTION

The present invention concerns an adjustable spinal instrument for pedicle fixing and makes it possible to adapt and re-establish the physiological curves of the spine.

BACKGROUND OF THE INVENTION

Generally speaking, joined pedicle screws are implanted by rods or plates, the screw in all cases being strictly perpendicular to the rod or plate.

SUMMARY OF THE INVENTION

The invention seeks to overcome this drawback and offers a rod fixing device enabling the rods to be adjusted with respect to the axis of the pedicle screws.

To this effect, the object of the invention is to provide a device for fixing spinal osteosynthesis rods on pedicle screws of the type including a diapason-shaped head defining two branches receiving a rod to be fixed, said rod being locked in its housing by a locking screw, wherein it further comprises, fitted onto the rod and inserted between the locking screw and the bottom of said housing, a split ring whose external opposing faces directed towards said locking screw and said bottom are convex and received in complementary concave surfaces provided on the extremity of the locking screw and the bottom of the receiving housing of the rod, said ring authorizing a certain angular clearance of the rod with respect to the axis of the screw prior to locking of the screw.

Such a device makes it possible to adjust the angle formed by the rod with the axis of the pedicle screw, especially in the sagittal plane, and to lock the rod in the desired position by virtue of the split ring which deforms and immobilizes the rod under the pressure of the locking screw.

BRIEF DESCRIPTION OF THE DRAWINGS

Other characteristics and advantages of the invention shall appear more readily from a reading of the following description of an embodiment of the device of the invention, this description being given solely by way of example and with reference to the accompanying drawings on which.

DETAILED DESCRIPTION OF THE DRAWINGS

Figure 1:
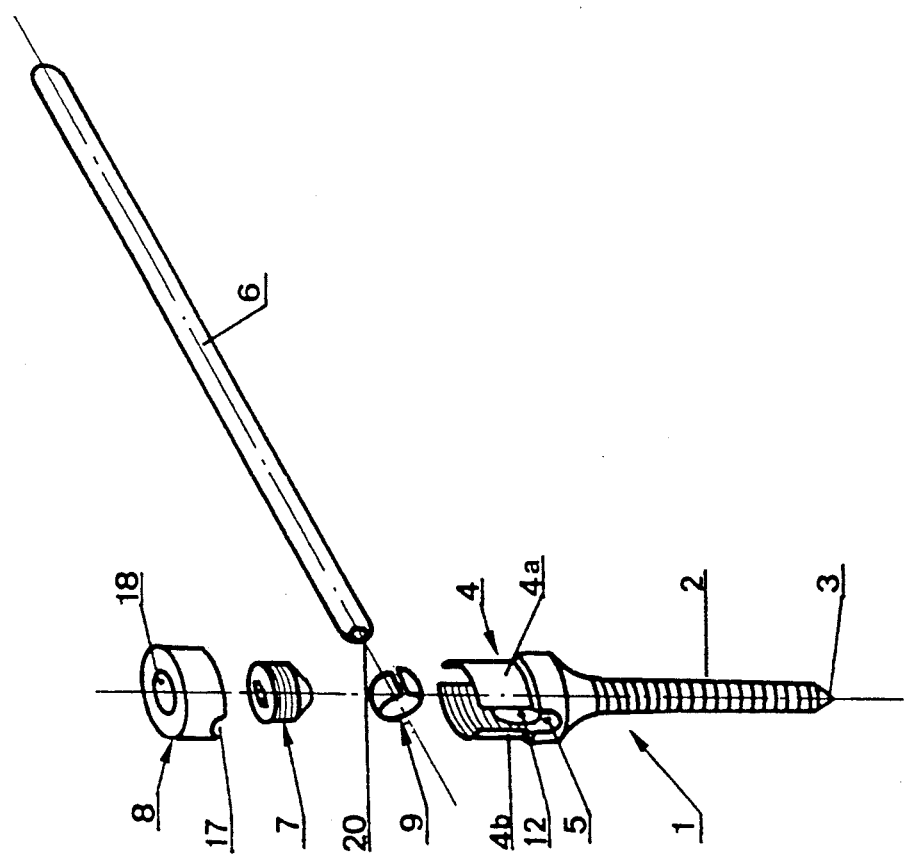
FIG. 1 is an exploded view of a device conforming to the invention.

FIG. 1 shows at 1 a known type of pedicle screw. It comprises a conical screw 2, an ogival point 3 and a diapason-shaped cylindrical head 4 pierced on both sides. More specifically, the head 4 comprises two opposing parallel branches 4a and 4b collectively defining a scalloping or housing 5 with a general axis perpendicular to the axis of the screw 2 and able to receive a generally cylindrically shaped rod or integralization element 6. Such a structure is well known and is described in the document GB-2.173.104, for example.

The opposing internal faces of the branches 4a and 4b are cylindrical and threaded in such a way as to receive a locking screw 7 for locking the rod 6 in its housing 5 in the same way as the screw locking device described in the document EP-0.010.527.

The head 4 receives a cap 8 covering the upper extremities of the branches 4a and 4b.

In accordance with the invention, locking of the rod 6 is ensured by means of a split ring 9 able to slide freely over the rod 6 received in the housing 5 and locked by the locking screw 7.

The ring 9, the extremity of the locking screw 7 and the portion of the housing 5 in contact with the ring 9 are made to conform with one another in a particular way.

Figure 3:
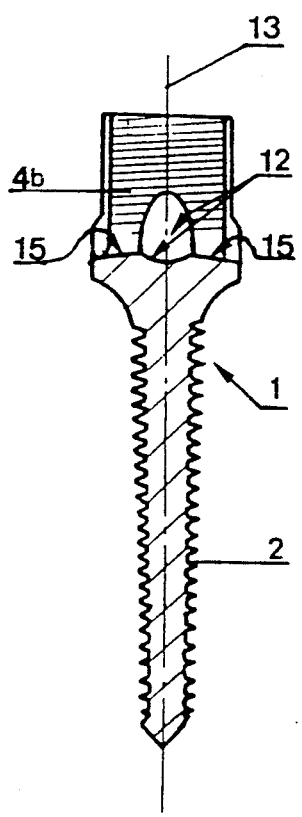
FIG. 3 is a section along the sagittal plane of a pedicle screw according to the invention.
Figure 4:
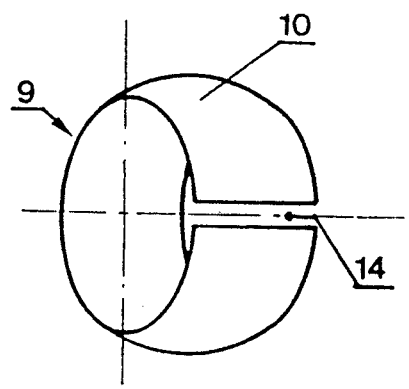
FIG. 4 is a perspective view of a split ring according to the invention.
Figure 6:
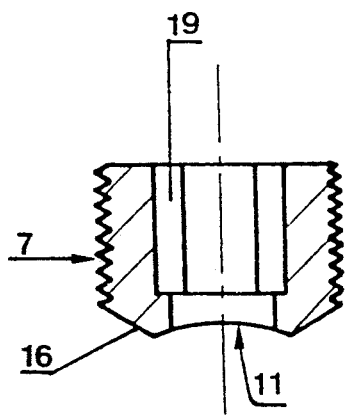
FIG. 6 is an axial cutaway view of a locking screw according to the invention.

In the embodiment represented, the ring 9 comprises (FIG. 4) an external spherical convex surface 10 cooperating firstly with a spherical concave surface 11 (FIG. 6) provided at the extremity of the conical section of the locking screw 7, and secondly with a spherical concave surface 12 (FIG. 3) provided in the bottom of the housing 5 to receive the rod 6 between branches 4a and 4b of head 4.

The ring 9 is disposed in such a way that its plane is approximately perpendicular (FIG. 2) to the sagittal plane of the screw 1, which is defined by the axis 13 of the screw and the general axis of the housing 5 receiving the rod 6.

Figure 5:
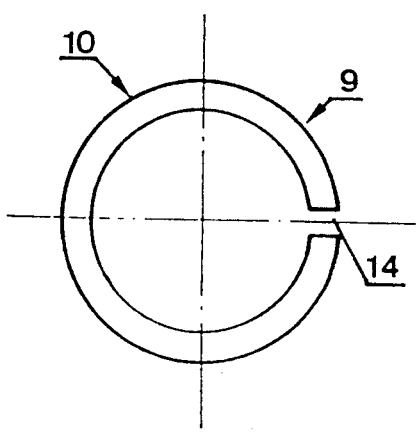
FIG. 5 is a lateral front view of the ring of FIG. 4.

The ring 9 is provided with a straight slot 14 (FIGS. 4 and 5) and has one internal cylindrical face 15 just slightly larger than the diameter of the rod 6.

Figure 2:
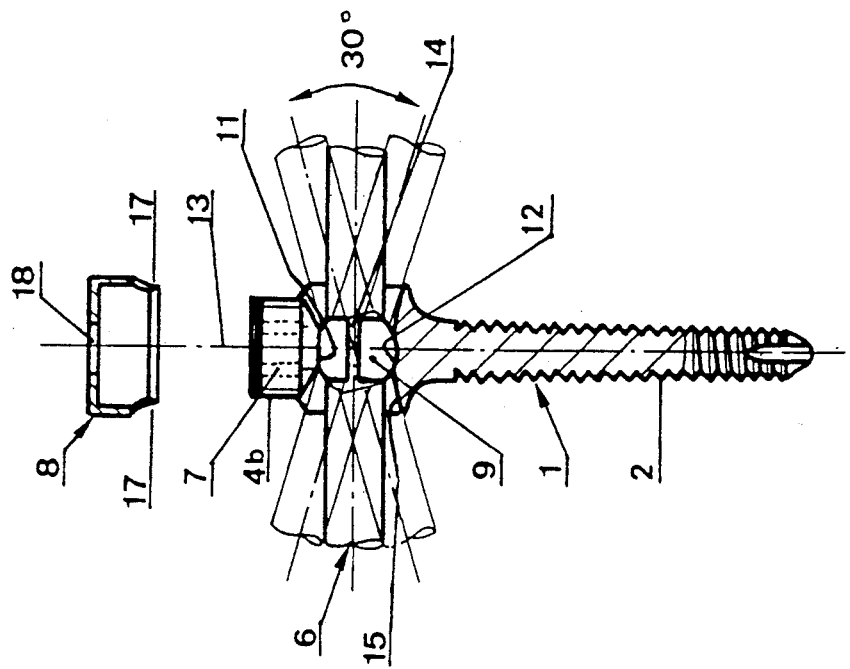
FIG. 2 shows the device of FIG. 1, the device being assembled except for the cap.

The rod 6 on which a ring 9 is fitted is inserted inside the housing 5 of the pedicular screw 1 after placing this screw in the appropriate bony portion. The ring 9 is engaged in the housing 5, 12 as shown on FIG. 2, then the locking screw 7 is screwed into the space between the branches 4a and 4b. Before locking the ring 9, the cap 8 is placed by simply being engaged astride the two branches 4a and 4b, then the rod 6 is suitably orientated inside the sagittal plane (FIG. 2) and locked with the desired orientation by compressing the split ring 9 with the locking screw 7. The angular clearance of the rod 6 is, for example, 15° around the position perpendicular to the axis 13 of the screw 1, as illustrated by FIG. 2.

When adjusting the rod 6, the ring 9 slides over the spherical surfaces 11 and 12 confining the rod.

So as to allow for the free angular clearance of the rod 6, the bottom of the housing 5 at the right of two opposing inlets is slightly recessed at 15 (FIGS. 2 and 3), the truncated section 16 of the point of the locking screw 7 (FIG. 6) ensuring the free clearance of the rod from the locking screw side.

The cap 8 comprises (FIG. 2) two opposing scallopings 17 for the free clearance of the rod 6 and a central piercing 18 for the passage of a wrench, such as a six-sided wrench, for tightening the locking screw 7 by means of a hollow six-sided recession 19 provided in the upper face of said screw 7.

The role of the cap is mainly to avoid spacing of the two branches 4a and 4b when tightening the locking screw. The cap 8 may be suppressed if the material of the screw 1 or the size of the branches 4a, 4b, especially relative to its thickness, so allows.

A thorough tightening of the locking screw 7 causes the rod 6 to be locked by the ring 9 in the selected position, the aperture 14 preferably being placed laterally, as shown on FIG. 2.

The rod is thus completely locked, both as regards its orientation and rotation around its axis.

The rod 6 may, for example, be a smooth interlocking element provided at its two extremities with a hollow six-sided recession (FIG. 7) or even an element made up of flexible plaited cylindrical strands.

By providing holes or recessions 20, this allows a complementary shaped wrench to be introduced with a view to acting on the derotation of the vertebral column.

In effect, by acting with wrenches on the rotation in the same direction of the rod 6 on its axis, this rod is made to rotate and accordingly the spline rotates along its vertical axis.

Finally, the invention is clearly not merely restricted to the embodiment described above, but covers all possible variants, especially as regards the shape and disposition of the convex and concave surfaces respectively of the ring 9 and the surfaces 11 and 12 between which it is screwed and as regards the locking screw 7 which may be screwed in the opposing branches 4a and 4b or in a piece mounted on the head 4 of the screw. Similarly, the shapes and dimensions of the ring 9 and the slot 14 may also vary without departing from the context of the invention to the extent that the slot plays the same role for elastic clamping the ring by crushing it on the rod to be locked.

Figure 7:
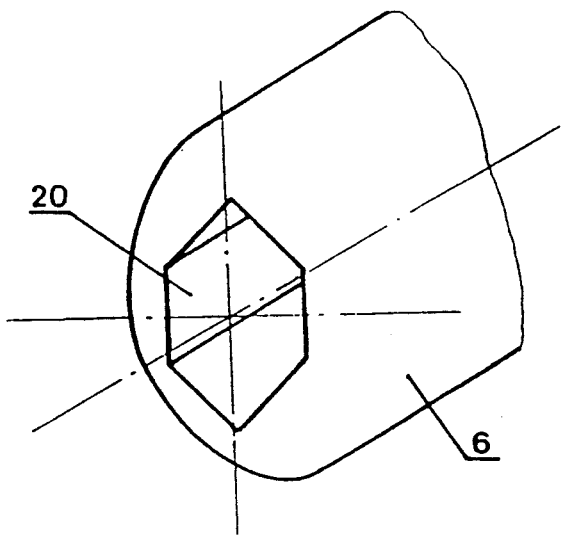
FIG. 7 is an enlarged view of the extremity of the rod of FIG. 1.

In addition, the extremities of the rod 6 may generally have an internal or external angular shape, as shown on FIG. 7, the contour of this shape able to be any, such as polygonal with n sides, and suitably-adapted to the contour of the wrench allowing the rod 6 to be rotated on its axis.

What is claimed is:

1. A device for fixing a spinal osteosynthesis rod, comprising:
    a pedicle screw having a diapason-shaped head with two spaced branches defining a housing for receiving a rod to be fixed therein, said housing having a bottom surface with a concave surface;
    a locking screw, coupled to said head, for blocking the rod in said housing, said locking screw having an end with a concave surface; and
    a split ring configured to be fitted onto the rod and inserted between said locking screw and said bottom surface of said housing, said ring having opposing external convex faces directed toward said locking screw and said bottom surface, respectively, said convex faces engaging and being complimentary to said concave surfaces of said bottom surface and said locking screw;
    whereby, said ring allows predetermined angular clearance of the rod relative to said pedicle screw prior to tightening of said locking screw.

2. A device according to claim 1 wherein said concave surfaces and convex faces are spherical.

3. A device according to claim 2 wherein said locking screw comprises a central truncated conical point defining said concave surface thereon.

4. A device according to claim 3 wherein said bottom surface of said housing has clearance recesses on opposite sides of said concave surface of said bottom surface in inlet areas of said housing, providing angular clearance for the rod.

5. A device according to claim 3 wherein a cap covers said branches of said pedicle screw and said locking screw, said cap having a central hole providing access to an operating recess in said locking screw.

6. A device according to claim 2 wherein said bottom surface of said housing has clearance recesses on opposite sides of said concave surface of said bottom surface in inlet areas of said housing, providing angular clearance for the rod.

7. A device according to claim 2 wherein a cap covers said branches of said pedicle screw and said locking screw, said cap having a central hole providing access to an operating recess in said locking screw.

8. A device according to claim 1 wherein said locking screw comprises a central truncated conical point defining said concave surface thereon.

9. A device according to claim 8 wherein said bottom surface of said housing has clearance recesses on opposite sides of said concave surface of said bottom surface in inlet areas of said housing, providing angular clearance for the rod.

10. A device according to claim 9 wherein a cap covers said branches of said pedicle screw and said locking screw, said cap having a central hole providing access to an operating recess in said locking screw.

11. A device according to claim 10 wherein said cap comprises opposing scallops on an edge thereof providing angular clearance for the rod.

12. A device according to claim 1 wherein said bottom surface of said housing has clearance recesses on opposite sides of said concave surface of said bottom surface in inlet areas of said housing, providing angular clearance for the rod.

13. A device according to claim 12 wherein a cap covers said branches of said pedicle screw and said locking screw, said cap having a central hole providing access to an operating recess in said locking screw.

14. A device according to claim 1 wherein a cap covers said branches of said pedicle screw and said locking screw, said cap having a central hole providing access to an operating recess in said locking screw.

15. A device according to claim 14 wherein said cap comprises opposing scallops on an edge thereof providing angular clearance for the rod.

16. A device according to claim 1 further comprising the rod fitted into said split ring, said rod having a recess for receiving a wrench to rotate said rod about a longitudinal axis.

* * * * *